US009329141B2

(12) United States Patent
Stutman et al.

(10) Patent No.: US 9,329,141 B2
(45) Date of Patent: *May 3, 2016

(54) LARGE FIELD OF VIEW GRATING INTERFEROMETERS FOR X-RAY PHASE CONTRAST IMAGING AND CT AT HIGH ENERGY

(71) Applicant: THE JOHNS HOPKINS UNIVERSITY, Baltimore, MD (US)

(72) Inventors: Dan Stutman, Cockeysville, MD (US); Michael Finkenthal, Columbia, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 159 days.

This patent is subject to a terminal disclaimer.

(21) Appl. No.: 14/176,655

(22) Filed: Feb. 10, 2014

(65) Prior Publication Data
US 2014/0226782 A1 Aug. 14, 2014

Related U.S. Application Data

(60) Provisional application No. 61/763,683, filed on Feb. 12, 2013.

(51) Int. Cl.
G01N 23/207 (2006.01)
G01N 23/04 (2006.01)
G01N 23/20 (2006.01)

(52) U.S. Cl.
CPC ............ *G01N 23/046* (2013.01); *G01N 23/207* (2013.01); *G01N 23/20075* (2013.01); *G01N 2223/419* (2013.01)

(58) Field of Classification Search
CPC .......... G01N 2223/419; G01N 23/046; G01N 23/20075; G01N 23/207
See application file for complete search history.

(56) References Cited

U.S. PATENT DOCUMENTS

| 4,798,446 A | 1/1989 | Hettrick |
| 5,812,629 A | 9/1998 | Clauser |
| 6,804,324 B2 | 10/2004 | Martynov et al. |
| 8,767,915 B2 * | 7/2014 | Stutman ................. G01N 23/04 378/156 |

(Continued)

FOREIGN PATENT DOCUMENTS

WO   WO 2013096974 A1 *  6/2013  ............... G21K 1/06

OTHER PUBLICATIONS international Search Report dated Oct. 16, 2014 from International Application No. PCT/US2014/033561, pp. 1-10.

(Continued)

*Primary Examiner* — David J Makiya
*Assistant Examiner* — John Corbett
(74) *Attorney, Agent, or Firm* — MH2 Technology Law Group LLP

(57) ABSTRACT

A device and method of the present disclosure provides large field-of-view Talbot-Lau phase contrast CT systems up to very high X-ray energy. The device includes microperiodic gratings tilted at glancing incidence and tiled on a single substrate to provide the large field-of-view phase contrast CT system. The present disclosure is a simple, economical, and accurate method for combining multiple GAIs into a larger FOV system, capable of performing phase-contrast tomography (PC-CT) on large objects. The device and method can be applied to medical X-ray imaging, industrial non-destructive testing, and security screening.

5 Claims, 12 Drawing Sheets

(56) References Cited

U.S. PATENT DOCUMENTS

| | | | |
|---|---|---|---|
| 2006/0002512 | A1 | 1/2006 | Cho et al. |
| 2007/0183579 | A1 | 8/2007 | Baumann et al. |
| 2009/0092227 | A1* | 4/2009 | David .................. A61B 6/4233 378/36 |
| 2010/0272235 | A1 | 10/2010 | Takahashi |
| 2012/0099702 | A1 | 4/2012 | Engel et al. |
| 2012/0099705 | A1 | 4/2012 | Murakoshi et al. |
| 2013/0028378 | A1 | 1/2013 | Stutman et al. |
| 2014/0226782 | A1* | 8/2014 | Stutman ............... G01N 23/046 378/4 |

OTHER PUBLICATIONS

Cai, Weixing et al. Dose efficiency consideration for volume-of-interest breast imaging using x-ray differential phase-contrast CT. Proc. of SPIE, 2009, vol. 7258, pp. 1-9.

Lauzier, Pascal T. et al. Interior tomography in x-ray differential phase contrast CT imaging. Phys. Med. Biol., 2012, vol. 57. pp. N117-N130.

Li, Ke et al. Differential phase contrast tomosynthesis imaging. Proc. of SPIE, 2012, vol. 8313, pp. 1-6.

Li, Jiangkun et al. Phantom Study for Volume-of-Interest Breast Imaging using Differential Phase Contrast Cone Beam CT (DPC-CBCT). Proc. of SPIE, 2013, vol. 8668, pp. 1-8.

Shimao, Daisuke et al. Shift-and-add tomosynthesis of a finger joint by X-ray dark-field imaging: Difference due to tomographic angle. European Journal of Radiology, 2008, vol. 68S, pp. S27-S31.

Stutman, D. et al. Glancing angle Talbot-Lau grating interferometers for phase contrast imaging at high x-ray energy. Applied Physics Letters, 2012, vol. 101, pp. 091108-1-091108-5.

Stutman, D. et al. High Energy X-ray Phase-Contrast Imaging Using Glancing Angle Grating Interferometers. Proc. of SPIE, 2013, vol. 8668, pp. 1-8.

Sunaguchi, N. et al. Refractive-index based tomosynthesis using dark-field imaging optics. Journal of Physics: Conference Series, 2013, vol. 425, pp. 1-5.

Zanette, I. et al Interlaced phase stepping in phase-contrast x-ray tomography. Applied Physics Letters, 2011, vol. 98, pp. 094101-1-094101-3.

International Search Report dated Apr. 30, 2015 from International Application No. PCT/US2015/011082, p. 1-15.

Zanette et al., "Interlaced phase stepping in phase-contrast x-ray tomography," Applied Phyisics Letters, 2011, vol. 98, pp. 094101-1 to 094101-3.

Cai et al., "Dose efficiency consideration for volume-of-interest breast imaging using x-ray differential phase-contrast CT," Proc. of SPIE, 2009, vol. 7258, pp. 1-9.

Lauzier et al., "Interior tomography in x-ray differential phase contrast CT imaging," Phys. Med. Biol., 2012, vol. 57, pp. N117-N130.

Li et al., "Differential phase contrast tomosynthesis imaging," Proc. of SPIE, 2012, vol. 8313, pp. 1-6.

Li et al., Phantom Study for Volume-of-Interest Breast Imaging using Differential Phase Contrast Cone Beam CT (DPC-CBCT), Proc. of SPIE, 2013, vol. 8668, pp. 1-8.

Shimao et al., "Shift-and-add tomosynthesis of a finger joint by x-ray dark-field imaging: Difference due to tomographic angle," European Journal of Radiology, 2008, vol. 68S, pp. S27-S31.

Stutman et al., "Glancing angle Talbot-Lau grating interferometers for phase contrast imaging at high x-ray energy," Applied Physics Letters, 2012, vol. 101, pp. 091108-1 to 091108-5.

Stutman et al., "High Energy x-ray phase-contrast imaging using glancing angle grating interferometers," Proc. of SPIE, 2013, vol. 8668, pp. 1-8.

Sunaguchi et al., "Refractive-index based tomosynthesis using dark-field imaging optics," Journal of Physics: Conference Series, 2013, vol. 425, pp. 1-5.

Arfelli et al., "Microbubbles as x-ray scattering contrast agents using analyzer-based imaging," Phys. Med. Biol., 55, 1643-1658 (2010).

Bech et al., "Hard x-ray phase-contrast imaging with the compact light source based on inverse Compton x-rays," J. Synchrotron Rad. 16, 43-47 (2009).

Bech et al., "Soft-tissue phase-contrast tomography with an x-ray tube source," Phys. Med. Biol., 54, 2747-2753 (2009).

Brey et al., "X-Ray Imaging of Poly(Ethylene Glycol) Hydrogels Without Contrast Agents," Tissue Eng. Part C. Methods, 16, 1597-1600 (2010).

Chapman et al., "Diffraction enhanced x-ray imaging," Phys. Med. Biol., 42, 2015-2025 (1997).

Coan et al., "Analyzer-based imaging technique in tomography of cartilage and metal implants: A study at the ESRF," European Journal of Radiology, 68, S41-S48 (2008).

Cornaby et al., "Silicon nitride transmission x-ray mirrors," J. Synchrotron Rad., 15, 371-373 (2008).

David et al., "Fabrication of diffraction gratings for hard x-ray phase contrast imaging," Microelectronic Engineering, 84, 1172-1177 (2007).

Donath et al., "Inverse geometry for grating-based x-ray phase-contrast imaging," J. Appl. Phys., 106, 054703 (2009).

Donath et al., "Toward Clinical X-ray Phase-Contrast CT—Demonstration of Enhanced Soft-Tissue Contrast in Human Specimen," Investigative Radiology, 45, 445-452 and suppl. pp. 1-6 (2010).

Donath et al., "Phase-contrast imaging and tomography at 60 keV using a conventional x-ray tube source," Rev. Sci. Instrum., 80, 053701 (2009).

Engelhardt et al., "The fractional Talbot effect in differential x-ray phase-contrast imaging for extended and polychromatic x-ray sources," Journal of Microscopy, 232, 145-157 (2008).

Hussein et al., "Modeling, validation and application of a mathematical tissue-equivalent breast phantom for linear slot-scanning digital mammorgraphy" Phys. Med. Biol., 54, 1533-1553 (2009).

Iida et al., "Synchrotron Radiation Excited X-Ray Fluorescence Analysis Using Wide Band Pass Monochromators," Nucl. Instrum. Meth. Phys. Res., A235, 597-602 (1985).

Joensen et al., "Multilayered supermirror structures for hard x-ray sycnhrotron and astrophysics instrumentation," Proc. SPIE vol. 2011 Multilayer and Grazing Incidence X-Ray/EUV Optics II, 360-372 (1994).

Kashyap et al., "Laboratory-based x-ray phase-contrast imaging technique for material and medical science applications," Applied Radiation and Isotopes, 66, 1083-1090 (2008).

Keyrilainen et al., "Phase-contrast X-ray Imaging of breast," Acta Radiologics, 8, 866-884 (2010).

Koch et al., "Refraction-enhanced x-ray radigraphy for inertial confinement fusion and laser-produced plasma applications," LLNL-JRNL-409414 J. Appl. Phys., 1-46 (2008).

Lawaczeck et al., "Monochromatic X-rays in Digital Mammography," Investigative Radiology, 40, 33-39 (2005).

Lewis, "Medical phase contrast x-ray imaging: current status and future prospects," Phys. Med. Biol., 49, 3573-3583 (2004).

Li et al., "Phase-sensitive x-ray imaging of synovial joints," Osteoarthritis and cartilage, 17, 1193-1196 (2009).

Mayo et al., "X-ray phase-contrast micro-tomography and image analysis of wood microstructure," Journal of Physics: Conference Series, 186, 012105 (2009).

Momose et al., "Phase Tomography by x-ray Talbot Interferometry," Instrumentation & Methodology, SPring-8, 144-145 (2006).

Muehleman et al., "Diffraction-enhanced imaging of musculoskeletal tissues using a conventional x-ray tube," Acad. Radiol., 16, 918-923 (2009).

Muehleman et al., "Multiple-image radiography for human soft tissue," J. Anat. 208, 115-124 (2006).

Park et al., "High-resolution 17-75keV backlighters for high energy density experiments," Physics of Plasmas, 15, 072705 (2008).

Park et al., "Quasi-monochromatic X-ray filter with thin film multilayer for a large area radiation field," Proc. SPIE 7258 Medical Imaging 2009: Physics of Medical Imaging, 72583L (2009).

Pfeiffer et al., "Phase retrieval and differential phase-contrast imaging with low-brillance x-ray sources," Nature Physics, 2, 258-261 (2006).

Pfeiffer et al., "Hard x-ray dark-field imaging using a grating interferometer," Nature Materials, 7, 134-137 (2008).

(56) References Cited

OTHER PUBLICATIONS

Rack et al., "Micro-imaging performance of multilayers used as monochromators for coherent hard x-ray synchrotron radiation," Proc. SPIE, vol. 7802, Advances in x-ray/EUV Optics and Components V, 78020M (2010).
Ress et al., "Novel xray imaging methods at the Nova Laser Facility (invited)," Rev. Sci. Instrum., 66, 579-584 (1995).
Reznikova et al., "Soft x-ray lithography of high aspect ratio SU8 submicron structures," Microsyst. Technol., 14, 1683-1688 (2008).
Sanchez Del Rio et al., "XOP: recent developments," 6 pages (1998).
Schuster et al., "Laterally graded multilayer optics for x-ray analysis," Proc. SPIE, vol. 3767, EUV, X-ray and Neutron Optics Sources, 183-198 (1999).
Shimao et al., "Shift-and-add tomosynthesis of a finger joint by x-ray dark field imaging: Difference due to tomographic angle," European Journal of Radiology, 68, S27-S31 (2008).
Stevenson et al., "Phase-contrast X-ray imaging with synchrotron radiation for materials science applications," Nuclear Instruments and Methods in Physics Research, B 199, 427-435 (2003).
Strobl et al., "Neutron Dark-Field Tomography," The American Physical Society, Phys. Rev. Lett., 101, 123902 (2008).
Stutman et al., "Development of optics for x-ray phase-contrast imaging of high energy density plasmas," Rev. Sci. Instrum., 81, 10E504 (2010).
Stutman et al., "Development of microperiodic mirrors for hard x-ray phase-contrast imaging," Applied Optics, 49, No. 25, 4677-4686 (2010).
Stutman et al., "Talbot phase-contrast x-ray imaging for the small joints of the hand," Phys. Med. Biol., 56, 5697-5720 (2011).
Suhonen et al., "Refraction and scattering of x-rays in analyzer based imaging," J. Synchrotron Rad., 14, 512-521 (2007).
Testorf et al., "Talbot effect for oblique angle of light propagation," Optics Communication, 129, 167-172 (1996).
Tommasini, "Development of backlighting sources for a Compton Radiography diagnostic of Inertial Confinement Fusion targets," LLNL-TR-429373 (2008).
Weitkamp, "XWFP: An x-ray wavefront propagation software package for the IDL computer language," Proc. SPIE 5536, 181-189 (2004).
Weitkamp et al., "Tomography with grating interferometers at low-brilliance sources," Proc. SPIE, 6318, 6318S (2006).
Wen et al., "Theory of oblique and grazing incidence Talbot-Lau interferometers and demonstration in a compact source s-ray reflective interferometer," Optics Express 19, 25093-25112 (Dec. 2011).
Woodard et al., "The composition of body tissues,"The British Journal of Radiology 59, 1209-1219 (1986).
Yuasa et al., "Highly sensitive detection of the soft tissues based on refraction contrast by in-plane diffraction-enhanced imaging CT," Nuclear Instruments and Methods in Physics Research, A 591, 546-557 (2008).
Zhou et al., "Development of phase-contrast x-ray imaging techniques and potential medical applications," Physics Medica 24, 129-148 (2008).

* cited by examiner

LARGE FIELD OF VIEW GRATING INTERFEROMETERS FOR X-RAY PHASE CONTRAST IMAGING AND CT AT HIGH ENERGY

CROSS REFERENCE TO RELATED APPLICATIONS

This application is related to U.S. patent application Ser. No. 13/493,392, titled "Differential Phase Contrast X-ray Imaging System and Components," filed on Jan. 31, 2013 and U.S. patent application Ser. No. 14/174,830, titled "System and Method for Phase-Contrast X-ray Imaging," filed on Feb. 6, 2014 by Dan Stutman and Michael Finkenthal, and claims priority from U.S. Provisional Patent Application 61/763,683 titled "High Energy X-Ray Phase Contrast CT Systems Using Tiled Glancing Incidence Gratings," filed on Feb. 12, 2013, hereby incorporated by reference in their entirety.

GOVERNMENT RIGHTS

This invention was made with government support under Grant No. 1R21EB012777-01A awarded by the Department of Health and Human Services, The National Institutes of Health (NIH). The government has certain rights in the invention.

FIELD

The present disclosure relates generally to medical imaging. More particularly the present disclosure relates to a device to provide large field-of-view phase contrast imaging with high energy X-ray.

BACKGROUND

A Talbot-Lau interferometer consists of three micro-period gratings: 'source', 'beam-splitter', and 'analyzer'. The source and analyzer are absorption grating typically made of Au, while the beam-splitter is a thin phase grating typically made of Si or Ni. To enable differential phase-contrast (DPC) imaging of thick body parts the interferometer must work at high energy. For instance, X-ray DPC imaging for the knee can potentially be done, for which radiography is typically done at 60-65 kVp (40-45 keV mean spectral energy) and conventional CT at 80-90 kVp (55-60 keV mean energy).

In addition, an interferometer must be very sensitive to small X-ray angular changes to enable refraction imaging with acceptable dose. The sensitivity is determined by two parameters: the fringe contrast or 'visibility' V, and the angular resolution, W. The contrast is defined as $V=(I_{BF}-I_{DF})/(I_{BF}+I_{DF})$, with $I_{BF}$ and $I_{DF}$ the 'bright-field' and the 'dark-field' intensity respectively, while W is given by the ratio between the interferometer period and the distance between the gratings. High contrast (in the ≥20% range approximately) is essential for medical DPC imaging, because the signal-to-noise ratio (SNR) in the DPC images improves rapidly with increasing contrast (e.g., as $\sim V^2$ in DPC-CT). Good angular resolution (W≤several μ-radian) is also needed, because the X-ray refraction angles in soft tissue are in the sub μ-radian range. The requirements for high contrast and angular resolution are more critical at high X-ray energy, because the refraction angles decrease with energy as $\sim 1/E^2$.

For DPC imaging of large body parts the Talbot-Lau interferometer must have ≥20% contrast at mean spectral energies ≥40 keV, while using gratings with ≤10 μm period. This is not possible however with the conventional normal incidence Talbot-Lau interferometer, because the thickness of few micron period absorption gratings is technologically limited to ~100 μm. To illustrate this limitation, in FIG. 1A, the computed contrast of a first Talbot order (m=1), 5 μm period interferometer designed for 55 keV mean energy, and having 100 μm thick, 50% duty-cycle Au gratings is plotted. Also plotted is the spectrum of an 80 kVp W anode tube after transmission through 2 mm Al, 75 μm Cu and 150 mm soft tissue. The maximal contrast is low and the contrast curve overlaps poorly with the tube spectrum, making for a spectrally averaged contrast of only ~6%. For comparison, an interferometer having perfectly absorbing gratings would have ~32% averaged contrast.

A device that enables phase contrast imaging at high X-ray energy is the glancing angle Talbot-Lau interferometer (GAI), in which the gratings have bars inclined at an angle α~10-30° along the beam direction. The effect of inclining the gratings is to increase the effective absorber thickness from the normal incidence value t, to $t/\sin(\alpha)$. Because the X-ray absorption increases exponentially with the thickness, this enables achieving high contrast at high energy using the existing ~100 μm thick gratings.

The main limitation of a GAI device, such as the one described above, is that the field of view in the direction perpendicular to the grating bars is limited (vignetted) to ≤few tens of mm by the strong collimation in the inclined grating openings, as illustrated in FIG. 1B. At the same time, an FOV of up to several tens of cm is needed for CT of larger objects such as thick body parts or checked baggage. In addition, previous research shows that the optimal configuration for phase-contrast tomography (PC-CT) is with the grating bars parallel to the CT axis, as in FIG. 1B.

It would therefore be advantageous to provide a device that combines in an efficient and accurate manner multiple GAI gratings so as to make large FOV interferometric systems that will allow DPC-CT and imaging of large objects.

SUMMARY

The foregoing needs are met, to a great extent, by the present disclosure, the interferometer also has multiple tiled micro-periodic gratings arranged on the substrate. The gratings include absorbing bars that are tilted at a glancing angle along the direction of the incident radiation. The absorbing bars are aligned parallel with the incident X-rays wherein the gratings have a fixed period along a grating bar direction.

According to an embodiment of the present disclosure, the interferometer device is configured for use in a large FOV DPC imaging system. The substrate can take the form of a single Si or C wafer. Multiple GAI gratings can be 'tiled' on the substrate and rotated to follow the X-ray beam direction as in FIG. 2, to achieve large horizontal FOV. Also, the gratings can be stacked in a vertical direction to make a large FOV in both the horizontal and vertical directions, to be used for DPC-CT or DPC radiography. The absorbing bars of the gratings are also inclined at an angle of approximately 10° to approximately 30° along the beam direction.

It is to be understood that both the foregoing general description and the following detailed description are exemplary and explanatory only and are not restrictive of the disclosure, as claimed.

Additional features, implementations, and embodiments consistent with the disclosure will be set forth in part in the description which follows, or may be learned by practice of the disclosure. The metes and bounds of the disclosure will be defined by means of the elements and combinations particularly pointed out in the appended claims.

BRIEF DESCRIPTION OF THE DRAWINGS

The accompanying drawings, which are incorporated in and constitute a part of this specification, illustrate embodiments of the disclosure and together with the description, serve to explain the principles of the disclosure. In the figures:

FIG. 4A shows a large FOV analyzer grating using three tiled wafers, FIG. 4B shows a side view of the scanner, and FIG. 4C shows a top view of the scanner.

DETAILED DESCRIPTION OF THE EMBODIMENTS

Reference will now be made in detail to exemplary embodiments of the disclosure, examples of which are illustrated in the accompanying drawings. Wherever convenient, the same reference numbers will be used throughout the drawings to refer to the same or like parts.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

A device and method of the present disclosure provides large field-of-view Talbot-Lau phase contrast CT systems up to very high X-ray energy. The device includes micro-periodic gratings tilted at glancing incidence and tiled on a single substrate to provide the large field-of-view needed for phase contrast CT systems. The present disclosure is a simple, economical, and accurate method for combining multiple GAIs into a larger FOV system, capable of performing phase-contrast tomography (DPC-CT) on large objects at high X-ray energy. The device and method can be applied to medical X-ray imaging, industrial non-destructive testing, and security screening.

X-ray differential phase-contrast (DPC) or refraction based imaging with Talbot-Lau grating interferometers has the potential to become a new medical imaging modality, offering improved soft tissue contrast and spatial resolution in comparison with conventional attenuation based imaging. In particular, recent analysis suggests that DPCCT could enable the detection of small lesions in soft tissue, which is not possible with other imaging modalities. New bone imaging modalities may also be possible.

Figure 2A:
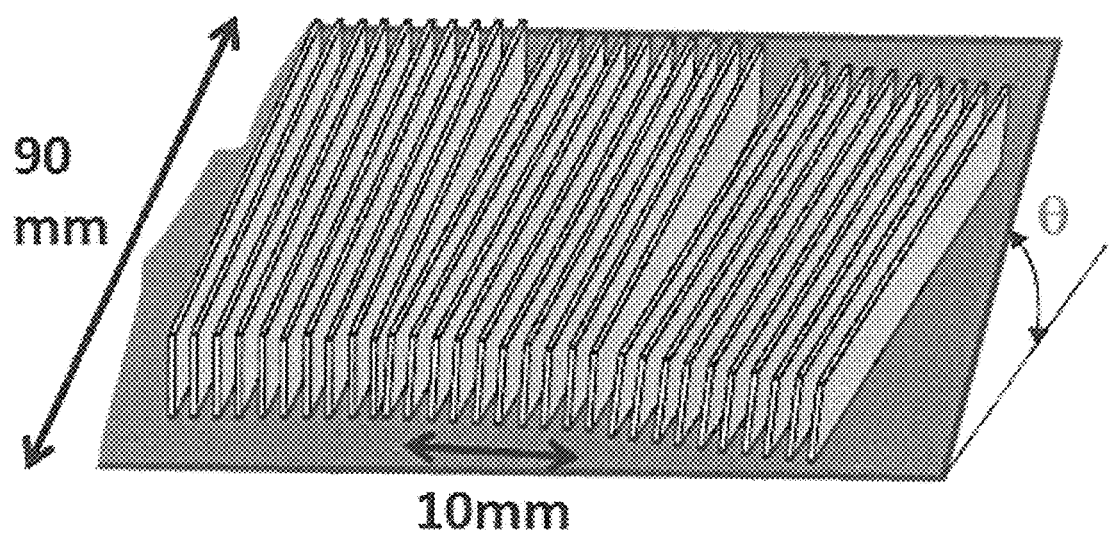
FIG. 2A illustrates a tiled glancing angle grating interferometer (GAI) having multiple grating blocks oriented parallel to the incident X-rays on a single substrate, according to an embodiment of the present disclosure.

The present disclosure includes use of multiple 'tiled' micro-periodic gratings having the absorbing bars tilted at a glancing angle along the direction of the incident radiation, and also aligned parallel with the incident X-rays, as illustrated in FIG. 2A. The tiling of the tilted gratings is an advancement over the Talbot-Lau Glancing Angle Interferometer (GAI), which will allow building in a simple and economical manner large FOV interferometric systems for DPC-CT with high energy X-rays.

The present disclosure also includes use of multiple tiled GAI gratings on a single substrate, as also shown in FIG. 2. The use of a single substrate strongly simplifies interferometer alignment and eliminates the need for many costly micro-positioning stages, since the 'sub-gratings' or grating blocks are pre-aligned with few nm precision through the lithographic manufacturing process.

FIG. 2A illustrates multiple tiled glancing angle grated interferometer (GAI) gratings on a single substrate, according to an embodiment of the present disclosure. As illustrated in FIG. 2A, multiple 'sub-gratings' or grating blocks with slightly rotated lines are positioned on a single substrate or wafer. All the sub-gratings have equal period and width; the width is equal or less than the FWHM of their vignetting curve (e.g., approximately 10 mm for a 10 µm period grating at 10° angle and having 2 m length). The rotation angle follows the central ray direction for each sub-grating. In this way, the incident X-rays 'see' an array of collimators that are with good approximation aligned to the ray direction, thus minimizing the vignetting. For instance, a 6" Si wafer would accommodate 12 sub-gratings of 10 mm width and 90 mm height, giving a FOV at the detector of 120 mm width and 30 mm height, at a glancing angle of 20°. Several such wafers side by side would cover a contiguous FOV of a few tens of cm wide, sufficient for full cone-beam CT of large objects.

An advantage in this solution is that the sub-gratings are aligned with nanometer precision through the lithographic manufacturing process, thus avoiding the need for complex and costly positioning systems.

Figure 3:
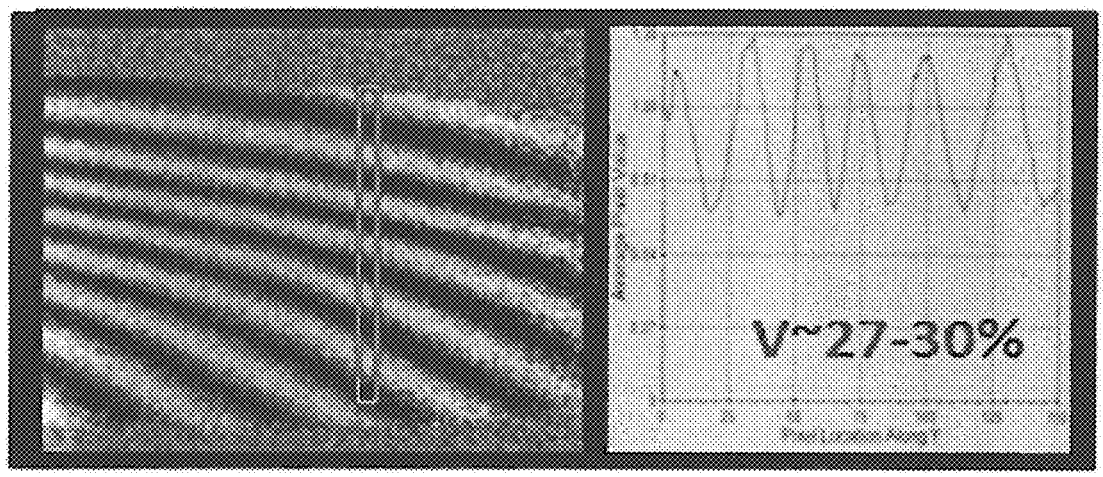
FIG. 3 illustrates Moiré fringes and high fringe contrast obtained with a GAI interferometer operated in 'tiled' mode.
Figure 4A:
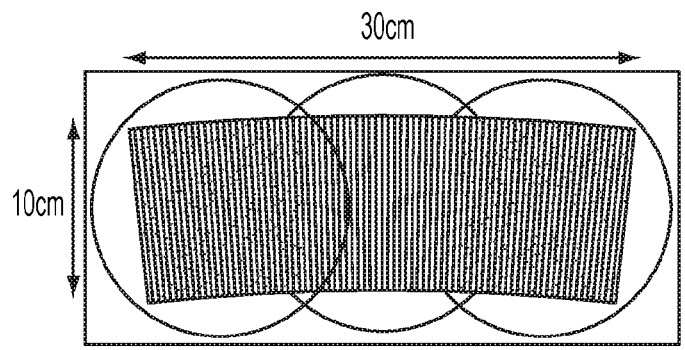
FIGS. 4A-4C shows an example design for a clinical scanner for large extremity joints consistent with embodiments of the disclosure, where
Figure 4B:
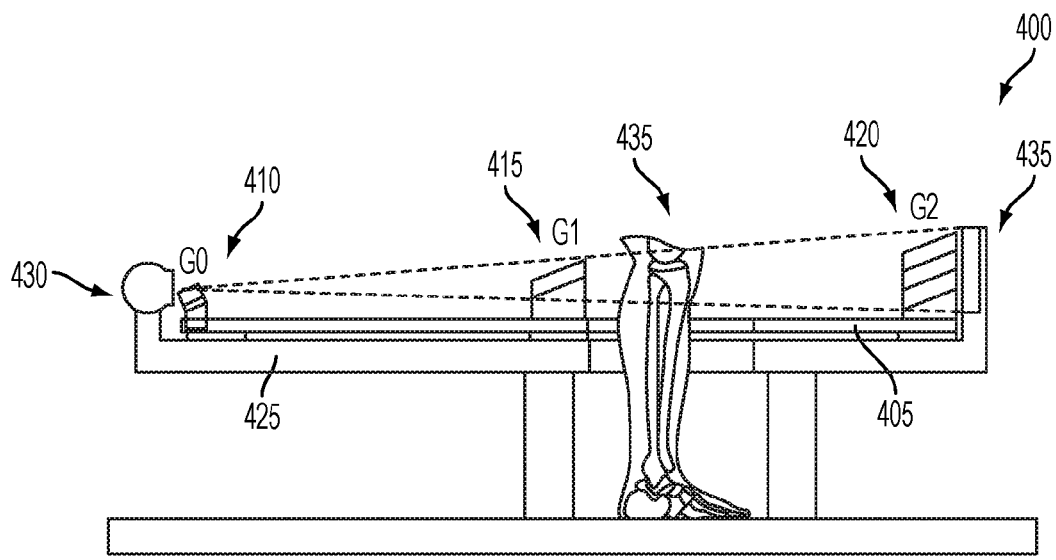
Figure 4C:
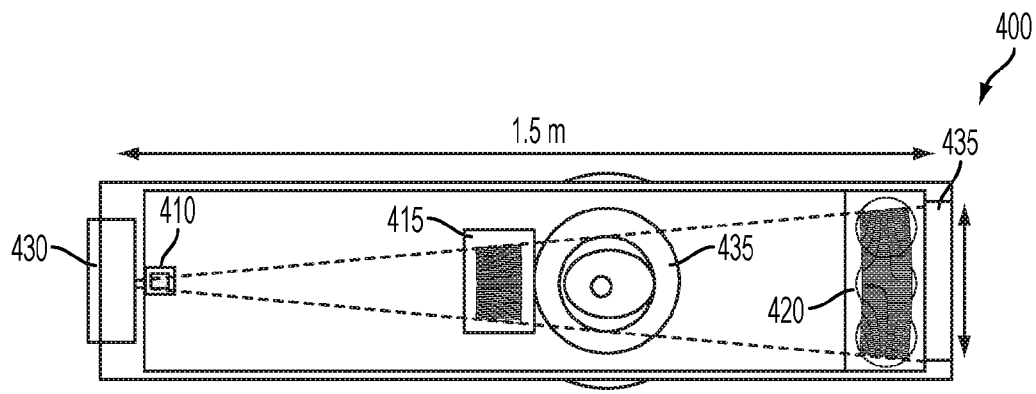

The functioning of the method in the present disclosure was experimentally tested by laterally translating and simultaneously rotating the gratings in a 10 μm period, 10° glancing angle interferometer of 2 m length. FIG. 3 illustrates the Moiré fringes and their contrast obtained in this setup, confirming that high interferometer contrast can be obtained with the gratings positioned far from the on-axis position. The tiled gratings can be further stacked in the vertical direction to make large horizontal and vertical FOV PC-CT systems, as illustrated in FIGS. 4A-4C. The tiled grating glancing angle interferometer offers thus a path towards the development of high energy DPC-CT systems, such as for CT of large extremity joints or head.

FIGS. 4A-4C show example views of a cone-beam GAI-CT scanner and imager that can be used for the clinical evaluation of extremity joints consistent with implementations of the present disclosure, where FIG. 4A shows a large FOV analyzer grating using three tiled wafers and FIGS. 4B and 4C show a side view and a top view of the scanner, respectively.

Figure 1A:
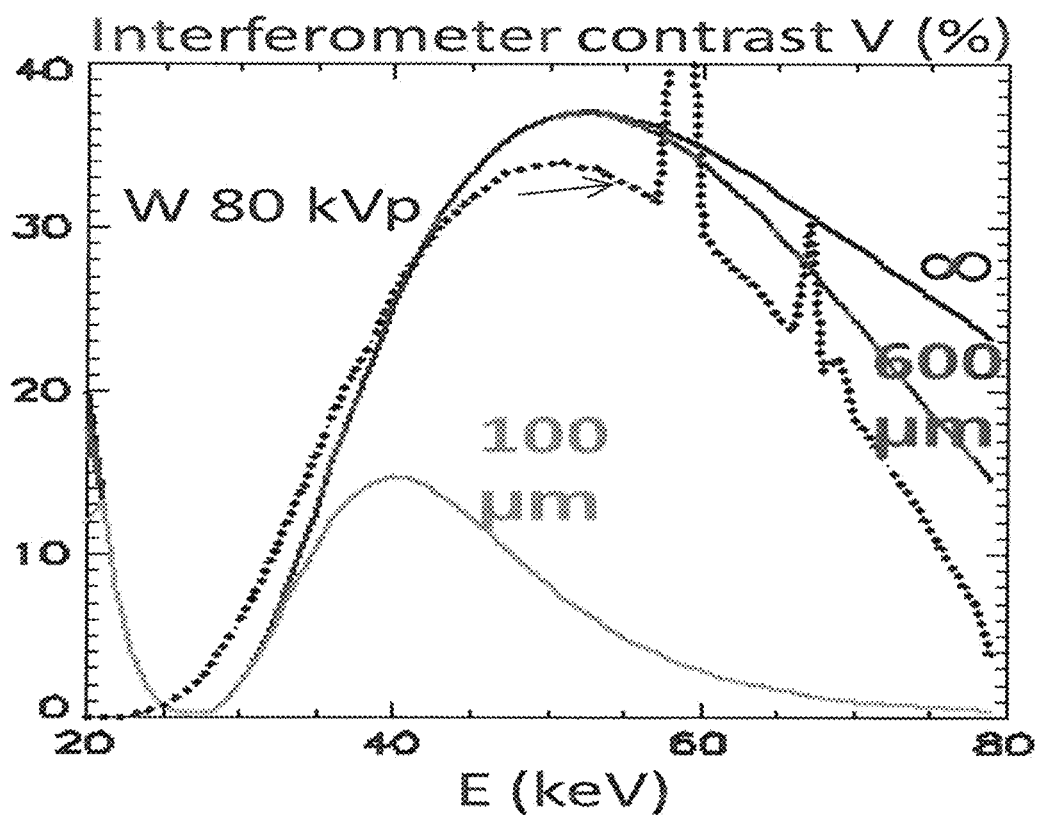
FIG. 1A illustrates a graphical view of the computed contrast of a first Talbot order (m=1), 5 µm period conventional (normal incidence) interferometer designed for 55 keV mean energy, and having 100 µm thick, 50% duty-cycle Au gratings (continuous gray line). Also shown the contrast for very thick gratings (∞), and for a GAI with the same gratings inclined at 10° angle (600 µm).
Figure 1B:
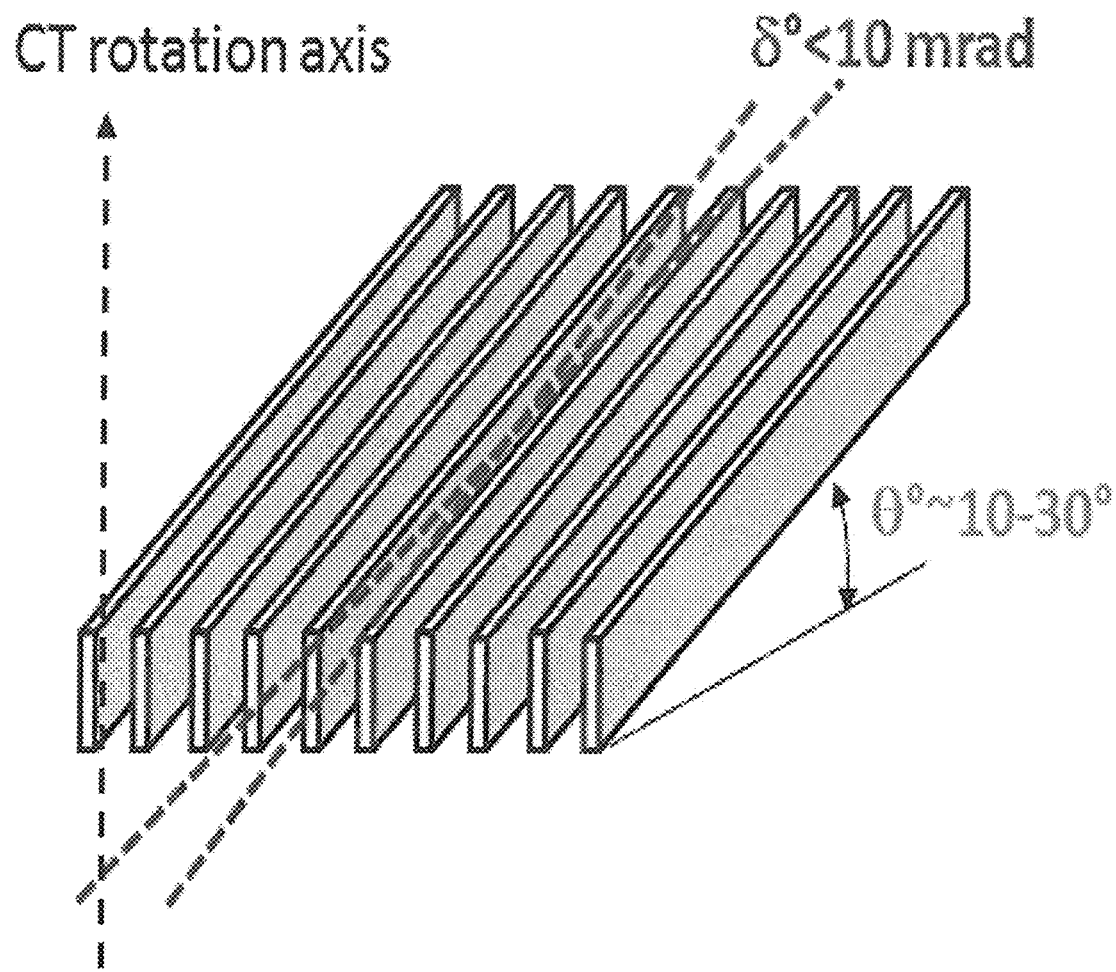
FIG. 1B illustrates grating bars for a GAI interferometer.

The system can work between 75-100 kVp, corresponding to transmitted spectra with 55-65 keV mean energy for the average human knee. This range encompasses that optimal for attenuation CT of extremities (80-90 kVp). To maximize the angular sensitivity while having a clinically compatible system length, the system uses a symmetric GAI design with gratings of equal period of about 5 μm, 100 μm thickness, and operated in the $3^{rd}$ Talbot order (~1.5 m length), at ~12° glancing angle. Calculations have shown that the $3^{rd}$ order maximizes the product of the angular sensitivity and contrast and thus the DPC-CT SNR. The computed fringe contrast as a function of energy is shown in FIG. 1A (curve marked 600 μm), indicating high spectrally averaged contrast of ~30%.

Figure 2B:
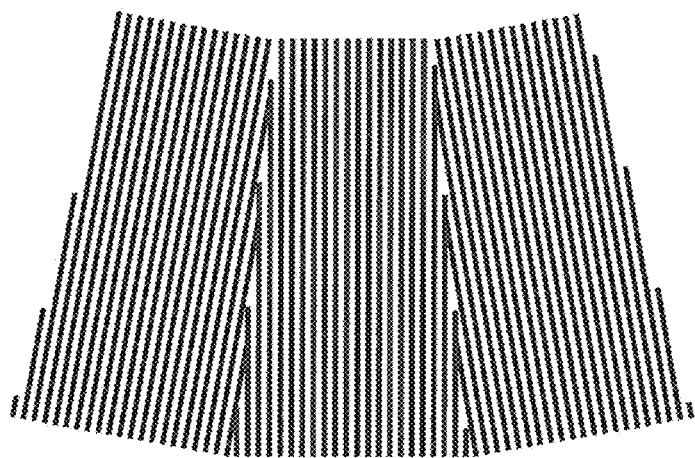
FIG. 2B shows an example arrangement of the sub-grating that are joined together in such a manner that the grating pattern is only slightly perturbed.

The design of a large area tiled grating is shown in FIG. 4A. A 30 cm wide by 20 mm tall FOV is achieved by overlapping three 6" wafers, carrying each a 100×100 mm tiled grating array composed of 10 sub-gratings of 10 mm width, inclined at 12°. The sub-gratings can be joined together in such a manner that the grating pattern is only slightly perturbed, as shown in FIG. 2B. For accurate positioning the wafers can be placed on a precision machined tray with clear apertures. The partial overlap between the grating substrates leads to only a small increase in beam attenuation. In some implementations, the tiled grating can have the fanned geometry, as shown in FIGS. 2A and 4A. In some implementations, the tiled GAI gratings are used to achieve a wide (e.g. 30 cm) FOV at the detector, while large FOV height is obtained by vertically stacking several rows of tiled GAIs. Alternately, 'slot-scan' DPC-CT systems can be built in which the object (e.g. a knee) is helically scanned with single row of GAI gratings.

FIGS. 4B and 4C show a side view and top view of the scanner 400, respectively. The scanner 400 includes a first arm 405 arranged to support the Talbot-Lau interferometer in a vibration free manner. The interferometer includes a source grating G0 410, a phase grating G1 415 and an analyzer grating G2 420. A second arm 425, separate from the first arm 405, is arranged to support the X-ray tube 430 and the detector 435. The first arm 405 and/or second arm 425 can be made of light, stiff, and thermally stable carbon honeycomb, such as used in space optics instrumentation as in known in the art. The scanner 400 can be mounted on a large bore stepper stage (not shown in detail) which will rotate it around a sample 435.

The X-ray tube 430 can be a dc tube instead of a pulsed one to eliminate the system or background phase variation due to pulsed X-ray heating of the source grating. An example of a suitable tube is the MXR-160HP/11 industrial tube made by Comet, Switzerland, delivering in dc mode up to ~25 mA at 80 kVp, and having dual spot capability (160 μm/400 μm in IEC336 standard). This X-ray tube provides a compact, light and vibration free X-ray source that is well suited for scanning together with the sensitive interferometer. Other similar type X-ray source could also be used as is known in the art.

The detector 435 can be a high efficiency, direct coupled CsI/CCD, such as the ARGUS model developed by Teledyne DALSA Inc. for panoramic imaging. This detector has about an order of magnitude higher sensitivity than a typical CMOS flat panel, and a wide form factor well suited for a slot-scan clinical system. The pixel size can be varied between 27-160 μm and the acquisition time is ≥0.125 s. Other similar type detectors could also be used as is known in the art.

The tiled GAI grating Talbot-Lau interferometer described with respect to the present disclosure can be directly applied for X-ray phase-contrast CT at high energy, without any further development. However, the design may be further optimized, particularly with respect to the sub-grating dimensions and angles, to physically demonstrate such systems, and to build prototypes for medical, security and NDT applications.

Figure 5:
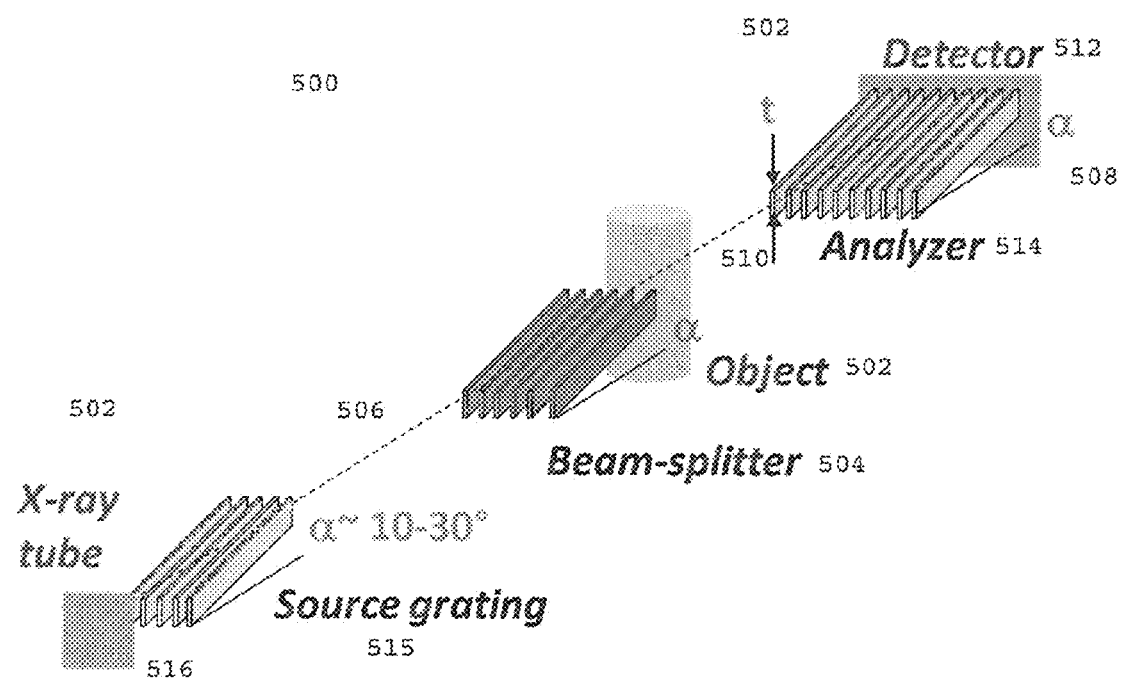
FIG. 5 illustrates a glancing angle Talbot-Lau interferometer using gratings with the bars inclined at an angle α~10-30° along the beam direction, according to an embodiment of the present disclosure.

Further with respect to the present disclosure, a glancing angle Talbot-Lau interferometer using gratings with the bars inclined at an angle α~10-30° along the beam direction, is illustrated in FIG. 5. The effect of inclining the gratings is to increase the effective absorber thickness from the normal incidence value t, to t/sin(α). Because the X-ray absorption increases exponentially with the thickness, this enables achieving high contrast at high energy using the existing ~100 μm thick gratings. The expected contrast improvement is illustrated in FIG. 1A with the computed contrast for the above interferometer assuming that the 100 μm Au gratings are inclined at an angle α~10° (600 μm effective thickness). The contrast strongly increases at high energy, leading to about a five-fold improvement in the spectrally averaged contrast.

Turning now to FIG. 5, an example schematic illustration of a differential phase contrast X-ray imaging system 500 is shown according to an embodiment of the present disclosure. The differential phase contrast X-ray imaging system 500 includes an X-ray illumination system 502, a beam splitter 104 arranged in an optical path 506 of the X-ray illumination system 502, and a detection system 508 arranged in an optical path 510 to detect X-rays after passing through the beam splitter 504. The detection system 108 includes an X-ray detection component 512. The beam splitter 504 includes a splitter grating arranged to intercept an incident X-ray beam and provide an interference pattern of X-rays. By way of a non-limiting example, beam splitter 504 can be a thin phase grating made of Si or Ni.

The detection system 508 also includes an analyzer grating 514 arranged to intercept and block at least portions of the interference pattern of X-rays prior to reaching the X-ray detection component 512. The analyzer grating 514 has a longitudinal dimension, a lateral dimension that is orthogonal to the longitudinal dimension, and a transverse dimension that is orthogonal to the longitudinal and lateral dimensions. The analyzer grating 514 has a pattern of optically dense regions, each having a longest dimension along the longitudinal dimension and spaced substantially parallel to each other in the lateral dimension such that there are optically rare regions between adjacent optically dense regions.

Each optically dense region has a depth in the transverse dimension that is smaller than a length in the longitudinal dimension. The analyzer grating 514 is arranged with the longitudinal dimension at a shallow angle α relative to incident X-rays such that the shallow angle α is less than 30 degrees. The longitudinal dimension of the analyzer grating 514 is oriented substantially along the optical path 510 (which can be the optical axis, for example), except tilted at the shallow angle α. (This will also be referred to as a glancing angle.)

In an embodiment of the current disclosure, each optically dense region has a depth in the transverse dimension that is smaller than a length in the longitudinal dimension by at least a factor of two. In an embodiment, each optically dense region has a depth in the transverse dimension that is smaller than a length in the longitudinal dimension by at least a factor of ten. In a further embodiment, each optically dense region has a depth in the transverse dimension that is smaller than a length in the longitudinal dimension by at least a factor of one hundred.

In an embodiment of the current disclosure, the shallow angle α is less than 25 degrees and greater than 5 degrees. In another embodiment, the shallow angle α is less than 15 degrees and greater than 3 degrees. An embodiment of the current disclosure is directed to medical applications. Since it is difficult to produce few-micron period gratings with more than ~100 μm Au absorber thickness, inclining the gratings at an angle in the 5-25° range makes for 200-1000 μm effective Au thickness. As is shown in FIG. 1A, this thickness enables >90% X-ray absorption (and thus high interferometer contrast) over the ~40 keV-110 keV energy range, of interest for medical phase-contrast imaging deep in the body. Another embodiment is directed to industrial or non-destructive testing (NDT) applications. Using glancing angles in the 3-15° range, the effective Au thickness is in the 400-2000 μm range, which makes for good X-ray absorption and interferometer contrast in the ~100 keV-250 keV energy range of interest for industrial NDT applications.

In an embodiment of the current disclosure, the splitter grating 504 is a reflection grating (not shown). In an embodiment of the current invention, the splitter grating 504 is a transmission grating. According to an embodiment of the current disclosure in which the splitter grating 504 is a transmission grating, similar to analyzer grating 514, such an embodiment of the analyzer grating has a longitudinal dimension, a lateral dimension that is orthogonal to the longitudinal dimension, and a transverse dimension that is orthogonal to the longitudinal and lateral dimensions. The splitter grating 504 in this embodiment has a pattern of optically dense regions, each having a longest dimension along the longitudinal dimension and being spaced substantially parallel to each other in the lateral dimension such that there are optically rare regions between adjacent optically dense regions. Each optically dense region has a depth in the transverse dimension that is smaller than a length in the longitudinal dimension. The splitter grating 504 is arranged with the longitudinal dimension at a shallow angle α relative to incident X-rays such that it is less than 30 degrees. In some embodiments, the splitter grating 504 can be similar in construction as the analyzer grating 514 and arranged similarly at a shallow angle α as described above with respect to the analyzer grating 514, although placed at a different position along the optical axis.

As used herein, the term "to block" X-rays is intended to mean that sufficient attenuation is achieved relative to X-rays that pass through the optically rare regions of the grating to permit a useful contrast for the particular application. It is not intended to require absolutely 100% attenuation.

The splitter grating 504 and the analyzer grating 514 are arranged with a separation determined according to Talbot-Lau conditions according to some embodiments of the present disclosure. In some embodiments, the splitter grating 504 and the analyzer grating 514 have grating patterns that are determined according to Talbot-Lau conditions.

The X-ray illumination system 502, according to some embodiments of the present disclosure can include an X-ray source 516, and a source grating 518 arranged in an optical path between the X-ray source 516 and the beam splitter 104. The source grating 518 provides a plurality of substantially coherent X-ray beams when X-ray source 516 is a spatially extended source of X-rays, as is illustrated schematically in FIG. 5. However, the broad concepts of the present disclosure are not limited to the particular embodiment illustrated in FIG. 5. The X-ray illumination system 502 can include combinations of one or more gratings and mirrors, including both transmission and/or reflection gratings. By way of a non-limiting example, the source grating 518 and the analyzer grating 514 are absorption gratings made of Au.

A limitation in the glancing angle design is that inclining the gratings reduces also the field of view in the vertical direction by of factor of $\sin(\alpha)$. Thus, assuming a typical grating height of ~70-80 mm, the achievable vertical field of view is ~12-40 mm for angles in the 10-30° range. In addition, a limitation common to all grating interferometers is that the horizontal field of view is reduced (vignetted) by the narrow (few μm), but deep (~100 μm) grating openings. At glancing incidence this effect is more pronounced due to the increased effective depth of the openings.

In exemplary experiments, a 'symmetrical' interferometer setup was used in which all grating periods are equal and the beam splitter is placed mid-distance between the source and the analyzer, this geometry provides maximal angular resolution for a given interferometer length. Two interferometers were used: (i) A 5.4 μm period m=3 interferometer having 100 μm thick Au gratings, 1.6 m total length, and operated at 18-30° glancing angle, with spectra having mean energy in the range 40-45 keV; and (ii) A 10 μm period m=1 interferometer having 120 μm thick Au gratings, having 2 m total length, and operated at 10-18° glancing angles, with spectra having mean energy in the range 55-58 keV. The gratings were made by MicroWorks Inc., Germany in 0.2-0.5 mm thick Si wafers and had 70 mm diameter. To obtain X-ray spectra with mean energy between 40 and 58 keV a W anode tube (1 mA/50 μm spot) was used at 60-80 kVp and immersed the samples to be imaged in a water bath having thickness between 70 and 200 mm. These conditions were meant to simulate imaging of a large joint such as the knee, while using relatively small test samples (the field of view of the interferometer at the sample being limited to 25 mm by the detector size and the 1.7 object magnification). The samples were positioned ~150 mm behind the phase grating.

Figures 6A, 6B, 6C:
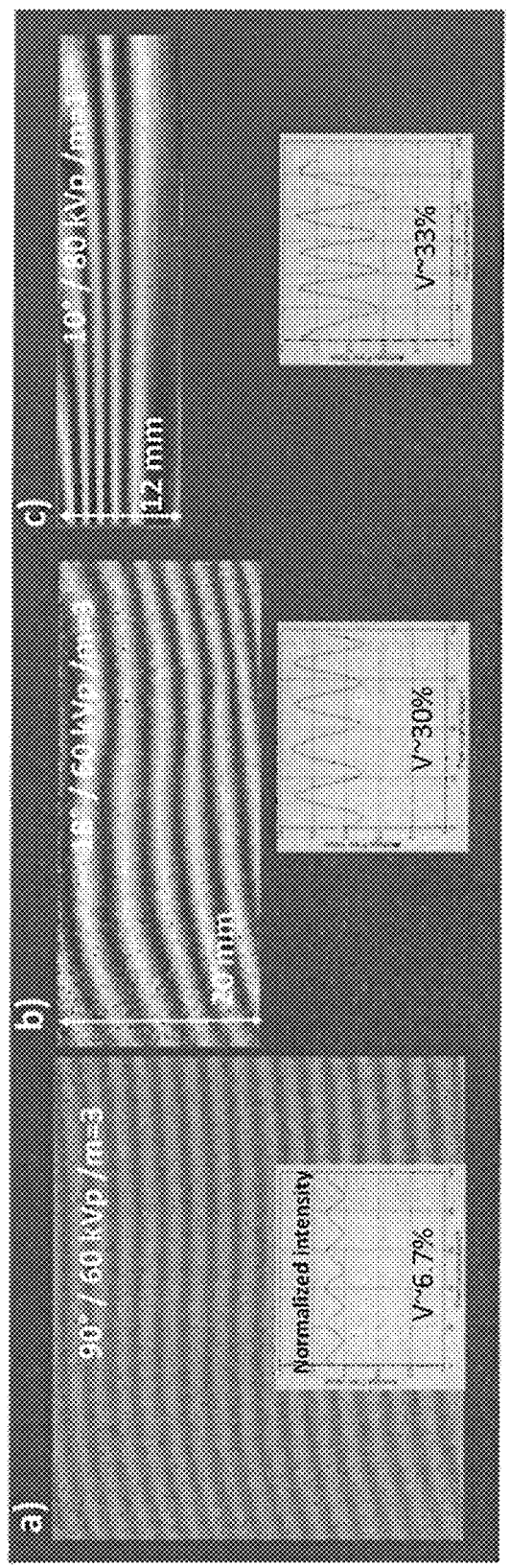
FIGS. 6A and 6B illustrate a large increase in contrast at high energy with the glancing angle interferometer, according to an embodiment of the present disclosure.
FIG. 6C illustrates the Moiré fringe contrast obtained at 80 kVp with X-rays passing through 20 cm of water, with a 10 µm period m=1 interferometer at 10° incidence, according to an embodiment of the present disclosure.

The detector was a 150 μm thick, 42×42 mm CsI:Tl scintillator, viewed by a 36×36 mm, 64-bit cooled CCD, through an f/1 relay lens system. The spatial resolution of the X-ray imaging system at the sample was ~75 μm. The low efficiency of the lens coupled detector and the low current of the X-ray tube required using long exposures (30-40 s) to acquire sufficient photon statistics. The large increase in contrast at high energy with the glancing angle interferometer is illustrated in FIGS. 6A and 6B. FIGS. 6A and 6B illustrate the Moiré fringe contrast obtained with the 5.4 µm interferometer and a 43 keV mean energy spectrum, at normal and at 18° incidence. At normal incidence the beam-splitter was an 8.5 µm thick Au grating, and at glancing incidence a 7 µm thick Ni grating. As seen, the glancing angle interferometer has several times the contrast of the normal incidence one. Even more encouraging for high energy DPC imaging is the result in FIG. 6C, which illustrates the Moiré contrast obtained at 80 kVp with the 10 µm period m=1 interferometer at 10° incidence. The spectrum was filtered with 2 mm Al, 0.65 µm Cu, and 200 mm water, to obtain a mean energy of ~58 keV. The 40-60 keV range of mean energies is particularly difficult for Talbot-Lau interferometry, because the Au X-ray absorption is low below 80 keV. The glancing angle setup enabled nevertheless achieving over 30% contrast even in this difficult region.

Figure 7:
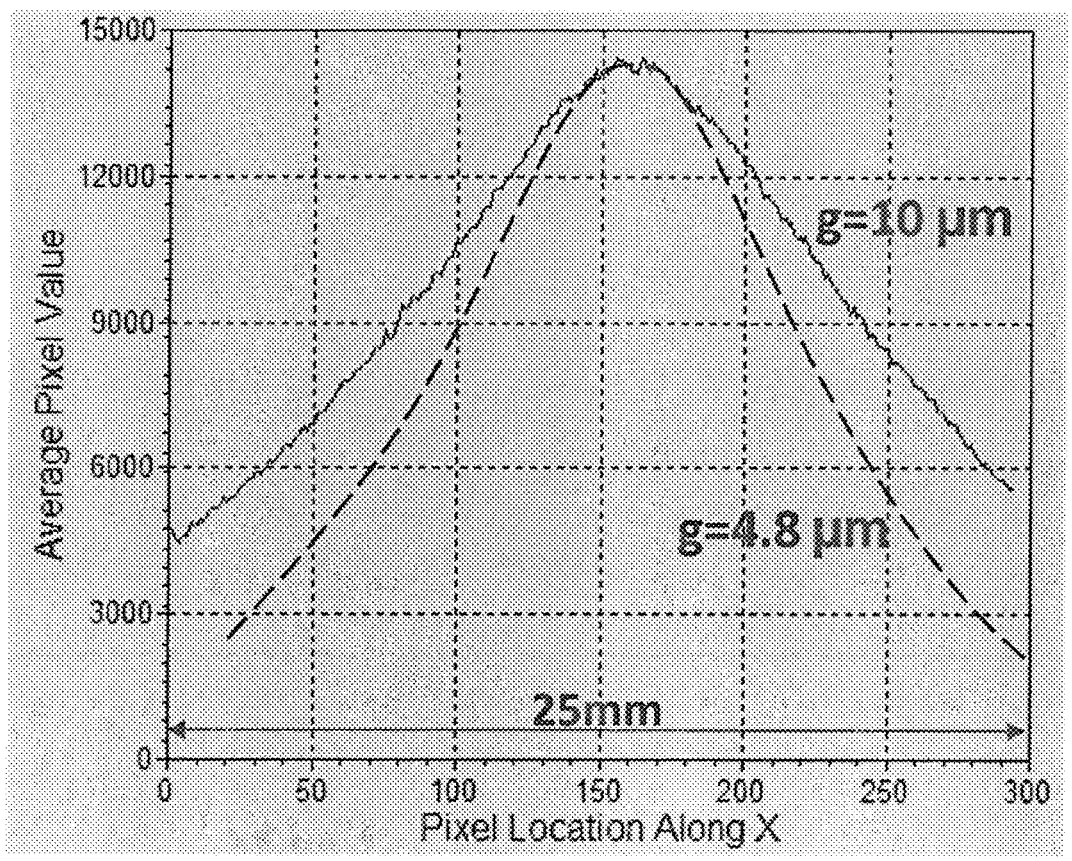
FIG. 7 illustrates the field of view vignetting that occurs in the GAI interferometer without tiling, according to an embodiment of the present disclosure.

Together with the contrast increase the vertical field reduction at glancing incidence is also apparent in FIGS. 6A, 6B, and 6C. Further on, the field of view vignetting at glancing incidence is illustrated in FIG. 7, which plots the horizontal intensity profile obtained with the 10 µm interferometer at 80 kVp/55 keV and at 10° glancing angle. The FWHM of the profile is only ~18 mm. For a smaller period/higher-m interferometer the FWHM further decreases, as illustrated by the horizontal intensity profile for a m=3, 2 m long interferometer having 4.8 µm period, 100 µm thick Au gratings at 10° angle. The X-ray transmission of the glancing incidence interferometer is in the 20% range, for instance ~21% peak transmission with the 5.4 µm interferometer at 18°, for a spectrum with 55 keV mean energy. The transmission could be increased by several percent using thinner grating substrates than in experiments.

Figure 8:
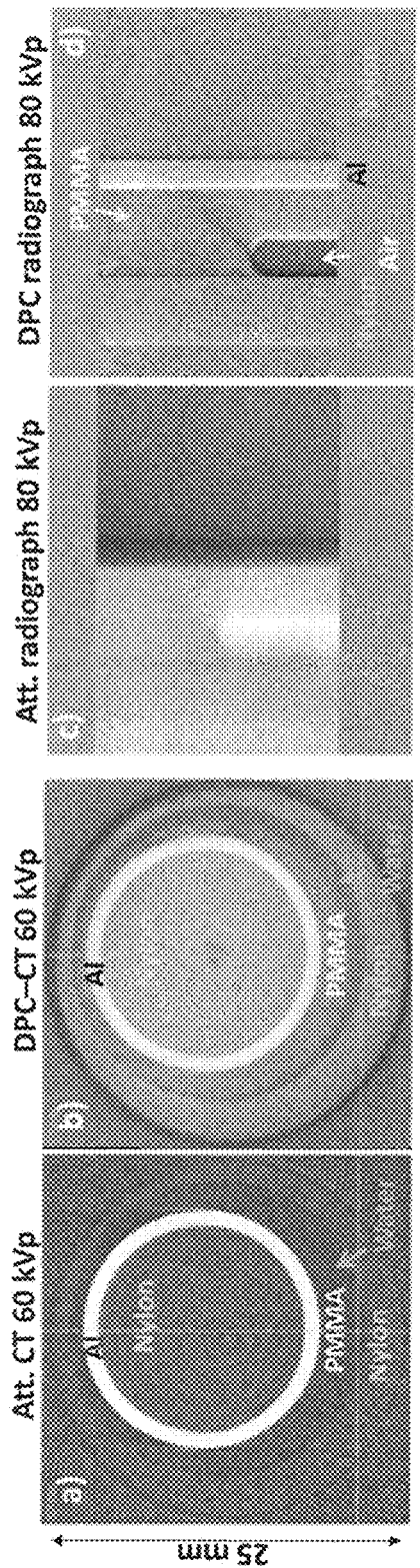
FIG. 8 illustrates images of a small joint phantom in water obtained with the GAI at high energy, according to an embodiment of the present disclosure.

For an assessment of the capability of an interferometer according to the present disclosure to discriminate materials resembling joint soft tissues, a phantom consisting of concentric cylindrical layers of water, PMMA, Al and nylon, simulating joint fluid, cartilage, cortical, and trabecular bone, respectively, was used, as illustrated in FIG. 8. As mentioned, to simulate the X-ray spectrum that would obtain when imaging a large joint the phantom was immersed in a thick water bath, with the water filling the interstices between layers.

Cone-beam CT images of the phantom were obtained at 60 kVp/43 keV mean energy with the 5.4 µm period interferometer at 30° and are illustrated in FIG. 8. The data was obtained using 200 CT angles with 1° step, 8 phase steps per angle and 30 s exposure per step. The results show that DPC-CT has superior discrimination capability for soft tissue like materials at high energy. For instance, DPC-CT discriminates PMMA (cartilage) from water, while attenuation CT does not. The nylon/water, and in particular the nylon/PMMA contrast is also superior in DPC-CT. In addition, fine details such as the thin interfaces between the layers have better contrast in DPC-CT. The 80 kVp DPC radiograph of the phantom immersed in 200 mm water also shows superior contrast compared to the attenuation one: the PMMA layer is discriminated in the DPC image but not in the attenuation one, and the nylon/water contrast is also strongly increased.

Figure 9A:
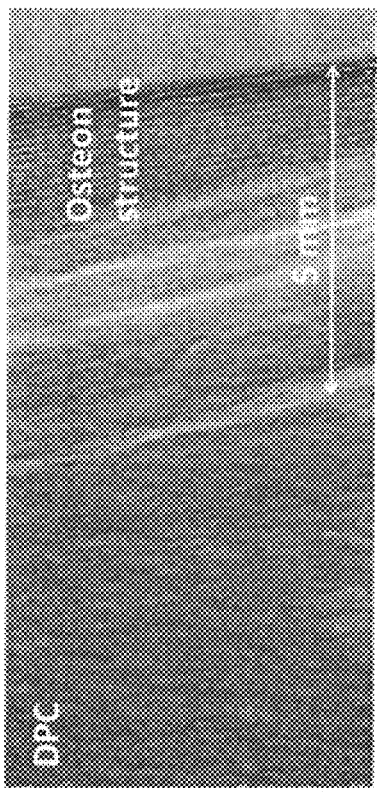
FIGS. 9A and 9B illustrate attenuation and DPC images of a ~40 mm diameter veal bone embedded in a whole veal leg, having ~120 mm thick muscle, obtained at 80 kVp energy with the GAI device, according to an embodiment of the present disclosure.
Figure 9B:
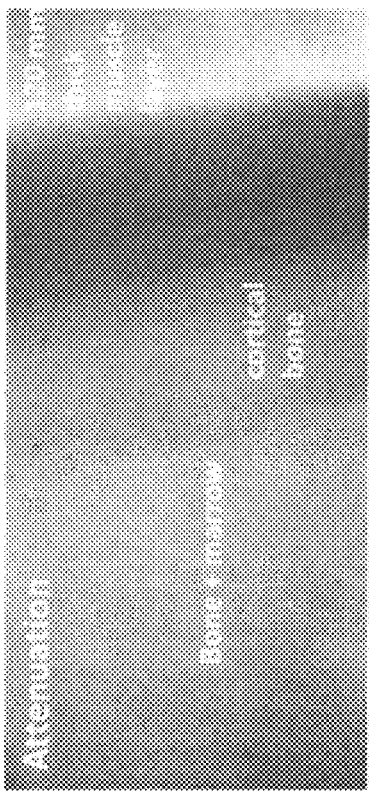

Bone poses a major challenge to medical DPC-CT because the strong small angle scattering (USAXS) in bone can lead to a substantial loss of interferometer contrast, to the point where DPC-CT in the presence of bone is no longer possible with the conventional interferometer. The high contrast of the glancing angle interferometer at high energy makes nevertheless possible phase contrast imaging in the presence of bone. The reason is twofold. First, at high enough energy the bone scatter decreases. Secondly, the initial contrast of the glancing angle interferometer is high enough that even after traversing a thick bone layer the X-rays remain sufficiently coherent to allow phase contrast imaging. This point is illustrated in FIGS. 9A and 9B with attenuation and DPC images of a ~40 mm diameter veal bone embedded in a whole veal leg, having ~120 mm thick muscle. The DPC image shows the fine osteon structure and possibly the periosteum layer of the cortical bone, which are not distinguishable in the attenuation image.

The glancing angle interferometer enabled also obtaining first DPC-CT images of a human joint with energetic X-ray spectra. Due to field of view limitations a human finger PIP joint of ~23 mm diameter was used, immersed in a 25 mm plastic vial. The vial was filled with a 60%-40% water ethanol mixture to preserve the tissue and further immersed in a thick water bath to produce an energetic transmitted spectrum. The CT parameters were the same as for the joint phantom experiments.

Figure 10:
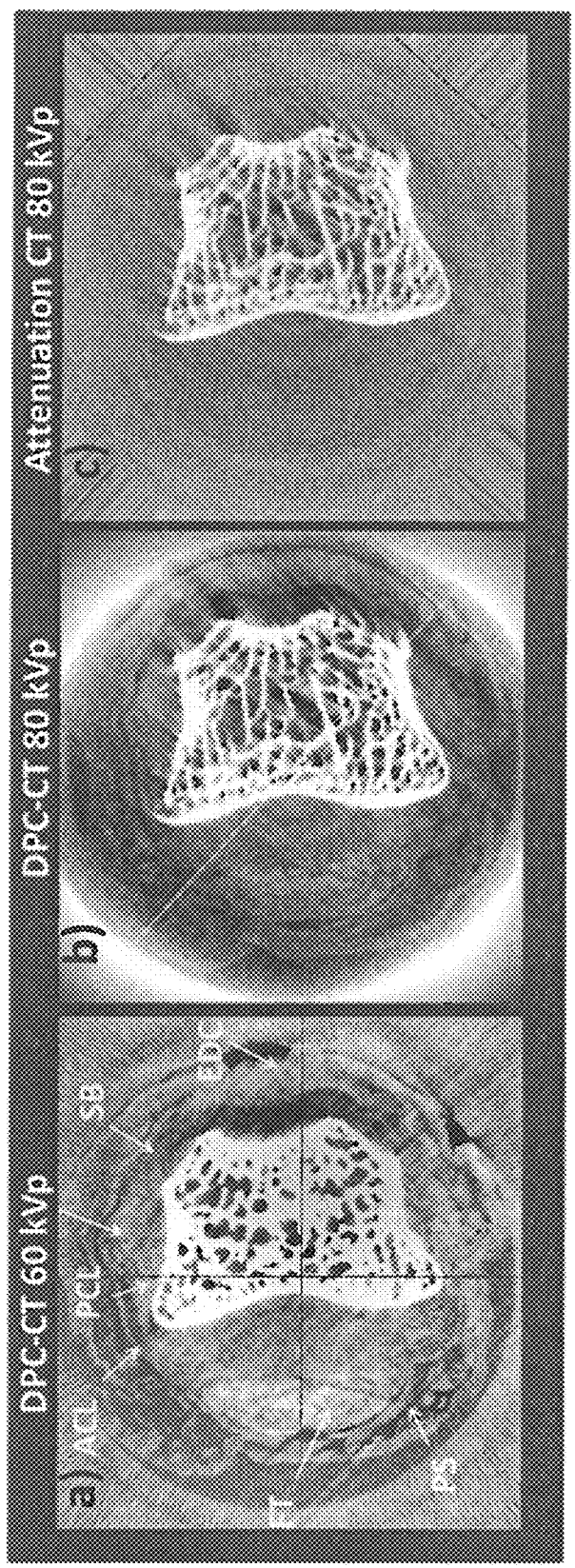
FIG. 10 shows DPC-CT and attenuation CT images of a human finger joint, obtained with 5.4 µm and with 10 µm glancing angle interferometers operated at 60 and 80 kVp respectively, according to an embodiment of the present disclosure.

FIG. 10 shows DPC-CT and attenuation CT images of the joint, obtained with the 5.4 µm and the 10 µm glancing angle interferometers at 60 and 80 kVp. Although noisy, the DPC-CT image shows soft tissue contrast at both 60 kVp and 80 kVp, while the attenuation CT image does not at either energy. The combination of soft tissue contrast and high spatial resolution in DPC-CT enables visualizing anatomical detail such as the flexor tendon (FT), the volar plate (FP), or the extensor digitorum communis (EDC).

The 80 kVp DPC image has somewhat less soft tissue contrast compared to the 60 kVp one, as expected from the decrease in refraction angles with energy and from the lower angular sensitivity of the 10 µm interferometer compared to the 5.4 µm one. Nevertheless, it is encouraging that it is possible to image soft tissues at high energy also with a larger period interferometer in the first Talbot order. This because larger period gratings can be made thicker, and because for a broad spectrum such as produced by a high kVp W tube the maximal interferometer contrast obtains in the first order.

The high frequency noise in the DPC-CT images appears due mainly to imperfections in the beam-splitter grating, while the low frequency noise appears due to slow system phase changes. These effects are exacerbated by long exposures, which make inaccurate subtracting the phase background measured at the beginning or at the end of a CT scan.

The above results show that the glancing angle grating interferometer offers a good solution for DPC imaging in the difficult region of 40-60 keV mean energy. The calculations further indicate that due to the increase in the Au absorption above 80 keV, this design offers high interferometer contrast up to ~150 kVp. In addition, encouraging for medical applications is that the soft tissue DPC contrast is superior to the attenuation one even at high energy, and that the glancing angle interferometer enables DPC imaging even in the presence of bone.

The combination of soft tissue contrast and high spatial resolution make the glancing angle interferometer of interest for clinical DPC imaging of thick body parts. The knee joint would be a good place to start studying clinical DPC imaging, because the knee can be kept fixed for relatively long periods of time and because physiological movement is less of an issue. A DPC-CT system for the knee should work in principle with a spectrum and patient exposure similar to that in conventional CT (80-90 kVp and <few hundred mA·s per scan, respectively).

The glancing angle interferometer solves the problem of the high energy contrast. Further on, the vertical field of view limitation of this instrument may be less constraining for knee CT, because imaging a 20-25 mm vertical region-of-interest centered on the joint space may be sufficient for most diagnostic purposes. However, the horizontal FOV must be much larger. Assuming a typical knee diameter of ~150 mm and an object magnification around 1.5, a FOV ≥220 mm would be needed at the detector for full cone-beam CT. The strong lateral vignetting of the glancing angle interferometer prevents however covering more than 10-20 mm with a single grating, as illustrated in FIG. 7.

The main question in the design of a glancing angle DPC-CT system is thus how to superimpose or 'tile' the gratings, so as to cover a large FOV in the horizontal direction. It is relatively easy to tile the gratings with the bars perpendicular to the CT axis. However, a preferable configuration for DPC-CT is with the grating bars parallel the CT axis, as illustrated in FIG. 5.

FIG. 4 shows an example implementation of the tiled grating GAI interferometer that includes using multiple 'sub-gratings' with slightly rotated lines, made on a single substrate or wafer. All the sub-gratings have equal period and width; the width is equal or less than the FWHM of their vignetting curve (e.g., 10 mm for a 10 μm period grating at 10° angle). The rotation angle follows the central ray direction for each sub-grating. In this way the incident X-rays 'see' an array of collimators that are with good approximation aligned to the ray direction, thus minimizing the vignetting. For instance, a 6" Si wafer would accommodate 12 sub-gratings of 10 mm width and 90 mm height, giving a FOV at the detector of 120 mm width and 30 mm height, at a glancing angle of 20°. Two such wafers side by side would cover a contiguous FOV 240 mm wide, sufficient for full cone-beam CT.

An advantage of the above example implementation is that the sub-gratings are aligned with nanometer precision through the lithographic manufacturing process, thus avoiding the need for complex and costly positioning systems.

The above example implementation was tested by laterally translating and simultaneously rotating the gratings in a 10 μm period, 10° glancing angle interferometer. FIG. 3 shows Moiré fringes obtained in this setup, confirming that high interferometer contrast is obtained also with the gratings positioned far from the on-axis position.

In conclusion, the tiled grating glancing angle interferometer offers a path towards the development of high energy DPC systems, such as for knee CT. Such systems might differ considerably from the conventional CT systems however. For instance, to achieve high spatial resolution at the object magnification of 1.5-1.7 typical for Talbot-Lau interferometry, the X-ray source may have a spot size in the 100 μm range. At the same time it may provide sufficient intensity to compensate the interferometer attenuation, and it may operate for extended periods because the DPC-CT scan times will likely be longer than in conventional CT. Such tubes nevertheless exist and could be adapted for clinical DPC-CT. For instance, microfocus rotating anode tubes have been developed for protein crystallography that have 70 μm spot size and can operate continuously at several kW power.

Detectors having simultaneously low noise, high efficiency and sensitivity, and large FOV in one dimension will also be needed. An example of such a detector is the ARGUS X-ray CCD developed by DALSA for panoramic dental imaging, which has a high resolution scintillator directly coupled to a 210 mm wide CCD. The high sensitivity and low noise of a direct coupled and cooled CCD would also help achieving high spatial resolution at acceptable patient dose. Photon counting detectors could be another option.

Estimates indicate that using such sensitive detectors in conjunction with single exposure phase-retrieval methods such as 'interlaced scanning' or Moiré interferometry, as are known in the art, it might be possible to perform high resolution DPC-CT at dose comparable to conventional CT. Recent analysis also suggests that DPC-CT should not require a higher X-ray flux than conventional CT. Due to the several fold intensity decrease in the gratings the scan time will be however inherently longer. In order to minimize the dose and scan time it will be thus important to try and apply to DPC-CT novel image reconstruction methods developed for conventional CT, such as model-based statistical reconstruction, sparse sampling, or compressed sensing, as are known in the art.

While the teachings has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method may be performed in a different order than illustrated or simultaneously. Furthermore, to the extent that the terms "including", "includes", "having", "has", "with", or variants thereof are used in either the detailed description and the claims, such terms are intended to be inclusive in a manner similar to the term "comprising." As used herein, the term "one or more of" with respect to a listing of items such as, for example, A and B, means A alone, B alone, or A and B. Those skilled in the art will recognize that these and other variations are possible within the spirit and scope as defined in the following claims and their equivalents.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. An interferometer device operable to condition incident X-rays in a high energy X-ray system comprising:
   a substrate;
   multiple tiled micro-periodic gratings arranged in a fan shape on the substrate, wherein the gratings comprise absorbing bars and the absorbing bars are tilted at a glancing angle along the direction of the incident X-rays, and wherein the absorbing bars are aligned parallel with the incident X-rays, over a width equal or less than their beam collimation or vignetting width.

2. The interferometer device of claim 1, wherein the device is configured for use with a large field-of-view (FOV) interferometric system.

3. The interferometer device of claim 1, wherein the substrate comprises a single substrate.

4. The interferometer of claim 1, wherein the gratings are tiled in a fan shape in the horizontal direction and stacked in a vertical direction to make a large horizontal and vertical field-of-view (FOV) differential phase-contrast tomography (DPC-CT) system.

5. The interferometer of claim 1, wherein the absorbing bars of the gratings are inclined at an angle of approximately 5° to approximately 30° along a propagation direction of the incident X-rays, and fanned on their substrate over an angle between approximately 5° and 15°, to make a large FOV X-ray interferometer for 50-150 kVp energy.

* * * * *